US00PP28193P2

(12) United States Plant Patent
Robacker et al.

(10) Patent No.: US PP28,193 P2
(45) Date of Patent: Jul. 11, 2017

(54) GRASS NAMED 'GOOD VIBRATIONS'

(50) Latin Name: *Schizachyrium scoparium*
Varietal Denomination: Good Vibrations

(71) Applicants: University of Georgia Research Foundation, Inc., Athens, GA (US); The United States of America, as Represented by the Secretary of Agriculture, Washington, DC (US)

(72) Inventors: Carol D. Robacker, Peachtree City, GA (US); Melanie L. Harrison, Griffin, GA (US)

(73) Assignees: University of Georgia Research Foundation, Inc., Athens, GA (US); The United States of Amercia, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/998,814

(22) Filed: Feb. 19, 2016

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Annette Para
(74) *Attorney, Agent, or Firm* — Klarquist Sparkman, LLP

(57) ABSTRACT

The new variety *Schizachyrium scoparium* 'Good Vibrations' is tough, adaptable, and drought tolerant with foliage that is purple and green from May to September; and with an upright to softly arching growth habit. The asexually reproduced variety is reliably propagated vegetatively.

9 Drawing Sheets

Latin name of the genus and species of the plant claimed: *Schizachyrium scoparium.*

Variety denomination: The new *Schizachyrium scoparium* claimed is of the cultivar denominated 'Good Vibrations'.

BACKGROUND OF THE INVENTION

The present invention relates to a new and distinct cultivar of *Schizachyrium scoparium* hereinafter referred to by the varietal domination 'Good Vibrations'.

The new *Schizachyrium* is a product of a planned breeding program conducted by the Inventors in Griffin, Ga. The objective of the *Schizachyrium* breeding program is to produce a tough and adaptable drought-tolerant plant with commercial value. This cultivar has significant commercial and home gardener appeal with its attractive foliage and low maintenance requirements. These and other qualities are enumerated herein.

Pedigree and history: In 2006, thirty-seven accessions (number of plants per accession ranged from one to 51 depending upon the germination of individual accessions) of *Schizachyrium scoparium* were germinated and transplanted into field plots in Griffin, Ga. After a two-year evaluation period, seeds from open pollination within accessions were collected and sown in 2008, yielding 368 seedlings. The 368 seedlings were evaluated in containers in a screenhouse in Griffin, Ga. A seedling from plant B19, was selected for further evaluation and labeled 'B19-23'. Seeds from open pollination were collected from 'B19-23' and were sown in spring 2009. The resulting seedlings were evaluated in containers in the screenhouse for two seasons. The new variety 'B19-23-78', now called 'Good Vibrations', was selected and was first asexually propagated in 2010 in Griffin, Ga. by root division, and planted into a field plot.

The new variety 'Good Vibrations' has been tested since 2011 in Griffin and Blairsville, Ga.

SUMMARY OF THE INVENTION

The following traits have been repeatedly observed and represent the characteristics of a new variety *Schizachyrium scoparium*, 'Good Vibrations'. The new variety 'Good Vibrations' has not been observed under all possible environmental conditions. The phenotype may vary somewhat with variations in, for example, temperature, day-length, light intensity, soil types, and water and fertility levels without, however, any variance in genotype.

Asexual reproduction of the new *Schizachyrium* 'Good Vibrations' by root division since 2010 has shown that the unique features of this new *Schizachyrium* are stable and reproduced true to type in successive generations.

'Good Vibrations' plants, along with the cultivars 'MinnblueA' (U.S. Plant Pat. No. 17,310) and 'Carousel' (U.S. Plant Pat. No. 20,948) have been evaluated since 2011 in field plots at Griffin, Ga. and Blairsville, Ga. Height from the soil to the tip of the flowering culm, height from the soil to the top of the foliage and width were collected each year from the Griffin plants. Foliage color was assessed monthly from May to September each year.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following traits have been consistently observed in the original plant of this new variety and in asexually propagated progeny grown from root divisions in Blairsville, and Griffin, Ga., and, to the best knowledge of the inventors, their combination forms the unique characteristics of the new variety 'Good Vibrations':

1. Foliage of 'Good Vibrations' is purple and green from May to September.
2. 'Good Vibrations' exhibits an upright to softly arching growth habit.

The new variety *Schizachyrium* 'Good Vibrations' can be compared to the cultivars 'Carousel' and 'MinnblueA'. Plants of the new *Schizachyrium* differ from 'Carousel' and 'MinnblueA' in the following characteristics:

1. The new variety 'Good Vibrations' exhibits similar total height to 'MinnblueA' and a greater total height than 'Carousel'.
2. The new variety 'Good Vibrations' has greater average foliage height than 'Carousel' and 'MinnblueA'.
3. The average canopy diameter of the new variety 'Good Vibrations' is narrower than the canopy diameter of 'MinnblueA'.
4. The new variety 'Good Vibrations' is different from 'Carousel' and 'MinnblueA' in foliage growth. The new variety 'Good Vibrations' has upright foliage transitioning to cascading foliage throughout the growing season, whereas 'Carousel' and 'MinnblueA' have mostly upright pointing foliage.
5. The new variety 'Good Vibrations' is different from 'Carousel' and 'MinnblueA' in foliage color. The foliage of the new variety 'Good Vibrations' is purple and green throughout the growing season, while the foliage of 'Carousel' and 'MinnblueA' is mostly green to green-blue.

The following observations, measurements, and values describe plants grown in Griffin, Ga. 'Good Vibrations' was propagated via root division and grown in one-quart containers prior to planting in field plots. All data are from plants established as single stem propagules in May 2011.

The new variety 'Good Vibrations' has colorful purple and green to yellow-green upright to cascading foliage throughout the summer, in contrast to the green to blue-green foliage of 'Carousel' and 'MinnblueA' (Table 1). 'Good Vibrations' was on average similar in height to 'MinnblueA'. 'Good Vibrations' displayed greater foliage height than 'Carousel' at test sites in Griffin, Ga. (Table 2). 'MinnblueA' exhibited the greatest foliage width of these three cultivars (Table 2). The new variety 'Good Vibrations' is observed to have a lower plant width to foliage height ratio than 'MinnblueA', 'Carousel', 'Blaze' (unpatented), 'The Blues' (unpatented) and 'Prairie Blues' (unpatented) and a lower plant width to total height ratio than 'Carousel', 'MinnblueA', and 'Blaze' (Table 3).

At the same age of development and under the same growing conditions 'Good Vibrations' is shorter in total height than 'Seasons in the Sun' (patent pending) and 'Cinnamon Girl' (patent pending).

'Seasons in the Sun' and 'Cinnamon Girl' have an upright rounded growth habit with cascading foliage from May to September, but the foliage of 'Good Vibrations' is upright in early summer, changing to cascading in midsummer.

Foliage colors vary during the growing season among these three cultivars. 'Good Vibrations' in early summer has Violet-Blue N92D, 'Seasons in the Sun' has Purple N77A or Purple 79A and 'Cinnamon Girl' has Purple N79C or Greyed-Purple 187A on the distal portion of the foliage. In mid-summer, while all three cultivars have various shades of Greyed-Purple on the distal portion of the leaves, 'Good Vibrations' also has Purple N77C. In late summer, both 'Cinnamon Girl' and 'Good Vibrations' have some Yellow-Green 144A leaves, while 'Seasons in the Sun' has some Green 138B leaves. Furthermore, 'Cinnamon Girl' has some Red-Purple 59A or Red-Purple 60C foliage, colors not seen in the other cultivars.

TABLE 1

Summary of foliage colors on upper leaf surface of 'Good Vibrations', 'MinnblueA', and 'Carousel' in July, August, and September 2014 on field plants in Griffin, GA. Number in parentheses indicates the percentage of leaves displaying primary color.

| Cultivar | Date | Primary Color | Secondary Color |
|---|---|---|---|
| 'Good Vibrations' | July | Greyed-purple 187A or N186C or Purple N77C on upper two-thirds of the leaf (100%) | Green 138B on lower third of foliage |
| | August | Greyed-Purple 183C or N186C (50%) | Yellow-Green 144A (50%) on entire leaf |
| | September | Purple N79B (50%) | Green 138A or 138B (50%) on entire leaf |
| 'MinnblueA' | July | Green N138B on entire leaf (80%) | Purple N77A on tips of foliage (20%) |
| | August | Green 137A (100%) | |
| | September | Green 137A (90%) | Greyed-Purple 183B (10%) |
| 'Carousel' | July | Green (100%) | |
| | August | Green 137B (100%) | |
| | September | Green 137A or 138A (100%) | |

TABLE 2

Total height, height to top of foliage and width of 'Good Vibrations' and two cultivars planted into a field plot in Griffin, GA. Data were collected on Nov. 20, 2014. Numbers in parentheses are the standard deviations.

| Cultivar | Number of reps | Total height (cm) (soil to tip of flowering stem) | Foliage height (cm) | Width (cm) |
|---|---|---|---|---|
| 'Good Vibrations' | 5 | 89.2 (6.4) | 40.4 (1.0) | 37.7 (8.8) |
| 'MinnblueA' | 4 | 95.0 (10.1) | 36.5 (5.9) | 61 (16.4) |
| 'Carousel' | 4 | 73.8 (17) | 24.5 (9.8) | 43.5 (9.7) |

In Table 2, total plant heights were measured from ground level to the tip of the highest flowering culm. Foliage width was measure twice on each plant, the first measurement being at the widest point and the second measurement perpendicular to the first. These measurements were made on Nov. 20, 2014, in Griffin, Ga. after four growing seasons. All measurements are in cm.

TABLE 3

Relationship of plant width to foliage height, plant width to total height and foliage height to total height of 'Good Vibrations' and five cultivars planted into a field plot in Griffin, GA. Measurements were made on Nov. 20, 2014 on five reps of 'Good Vibrations', four reps of 'MinnblueA', and 'Carousel', and one plant each of 'Blaze', 'The Blues', and 'Prairie Blues'. Numbers in parentheses are the standard deviations.

| Cultivar | Plant width/Foliage height | Plant width/Total height | Foliage height/Total height |
|---|---|---|---|
| 'Good Vibrations' | 0.93 (0.19) | 0.42 (0.08) | 0.45 (0.03) |
| 'MinnblueA' | 1.65 (0.22) | 0.64 (0.12) | 0.38 (0.02) |
| 'Carousel' | 1.87 (0.34) | 0.60 (0.12) | 0.33 (0.08) |
| 'Blaze' | 1.20 | 0.58 | 0.49 |

TABLE 3-continued

Relationship of plant width to foliage height, plant width to total height and foliage height to total height of 'Good Vibrations' and five cultivars planted into a field plot in Griffin, GA. Measurements were made on Nov. 20, 2014 on five reps of 'Good Vibrations', four reps of 'MinnblueA', and 'Carousel', and one plant each of 'Blaze', 'The Blues', and 'Prairie Blues'. Numbers in parentheses are the standard deviations.

| Cultivar | Plant width/Foliage height | Plant width/Total height | Foliage height/Total height |
|---|---|---|---|
| 'The Blues' | 1.50 | 0.44 | 0.30 |
| 'Prairie Blues' | 1.53 | 0.43 | 0.28 |

In Table 3, the relationship between foliage height and plant width is presented.

In summary, 'Good Vibrations' has more varied foliage color than 'Carousel' and 'MinnblueA' but is taller in total height than 'Carousel' and a little shorter in total height than 'MinnblueA'. 'Good Vibrations' and 'Carousel' are narrower than 'MinnblueA' in foliage width. 'Good Vibrations' is upright and rounded, with foliage height being close to width, in early summer while both 'Carousel' and 'MinnblueA' are broadly rounded, displaying width greater than foliage height. By late summer, 'Good Vibrations' displays cascading foliage with foliage width being less than half of the total height; while width of 'MinnblueA' and 'Carousel' is over half of their total height.

BRIEF DESCRIPTION OF THE FIGURES

FIGS. 4 and 5 are photographs of a plant of a 'Good Vibrations' plant taken on Jun. 8, 2012 in Griffin, Ga.; with FIG. 5 being an enlarged view.

FIGS. 8 and 9 are, respectively, photographs of a 'Good Vibrations' plant taken on Jul. 1, 2015, in Griffin, Ga.; with FIG. 9 being an enlarged view.

FIGS. 10 and 11 are, respectively, photographs of 'Carousel' (FIG. 10) and 'MinnblueA' (FIG. 11) plants taken on Jul. 1, 2015, in Griffin, Ga.

FIGS. 14 and 15, respectively, are photographs of 'Carousel' (FIG. 14) and 'MinnblueA' (FIG. 15) plants, taken on Aug. 22, 2012, in Griffin, Ga.

FIGS. 16 and 17 are photographs of a 'Good Vibrations' plant taken on Sep. 10, 2014, in Griffin, Ga.; with FIG. 17 being an enlarged view.

FIGS. 18 and 19 are, respectively, photographs of 'Carousel' (FIG. 18) and 'MinnblueA' (FIG. 19) plants taken on Sep. 10, 2014, in Griffin, Ga.

BOTANICAL DESCRIPTION

Figure 1:
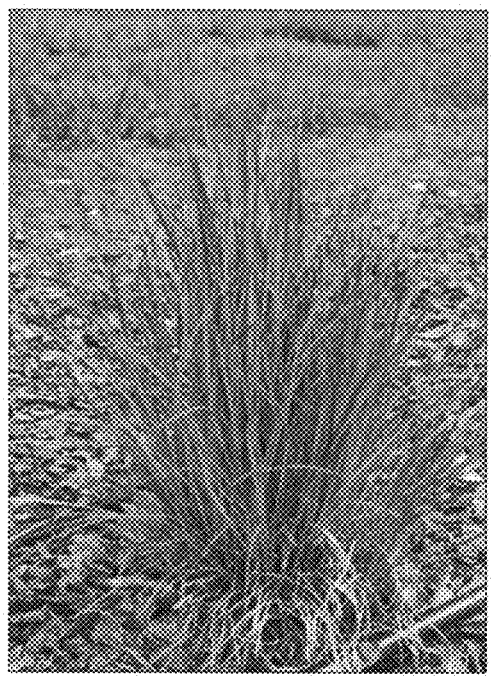
FIG. 1 is a photograph of a 'Good Vibrations' plant taken on May 26, 2015 in Griffin, Ga.
Figure 2:
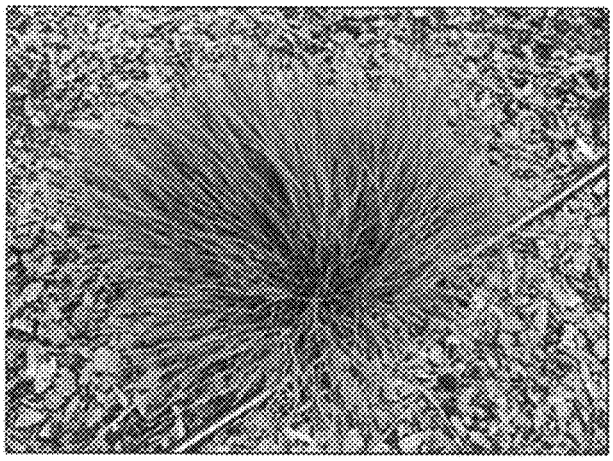
FIGS. 2 and 3 are, respectively, photographs of a 'Carousel' plant (FIG. 2) and of a 'MinnblueA' plant (FIG. 3), taken on May 26, 2015 in Griffin, Ga.
Figure 3:
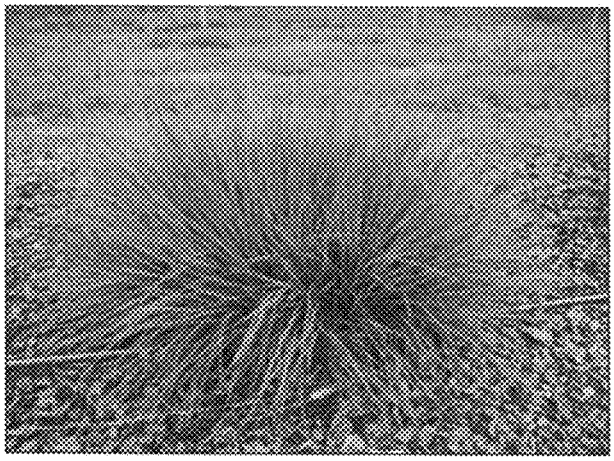
Figure 6:
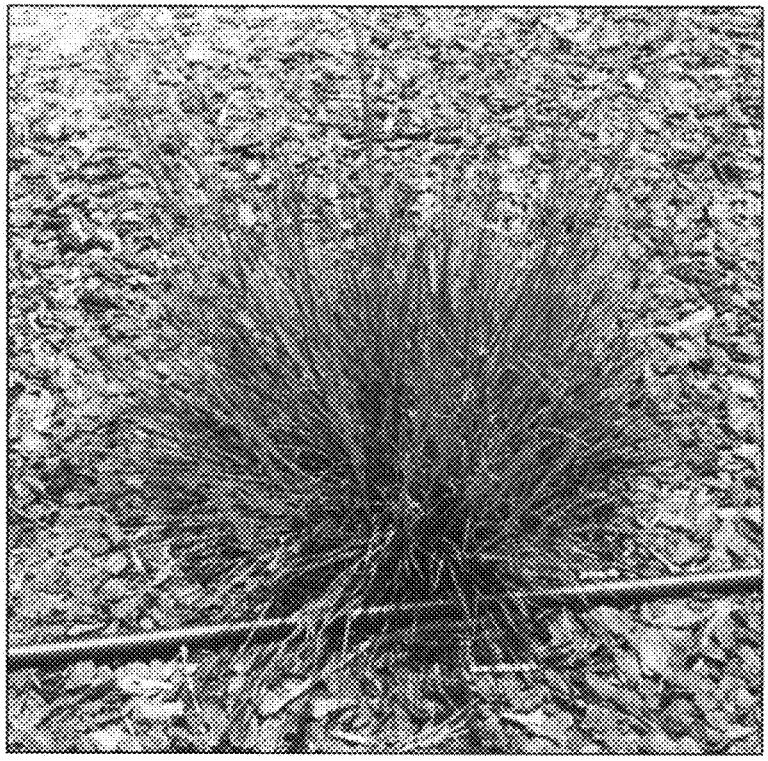
FIGS. 6 and 7 are, respectively, photographs of a 'Carousel' plant (FIG. 6) and a 'MinnblueA' plant (FIG. 7) taken on Jun. 8, 2012 in Griffin, Ga.
Figure 7:
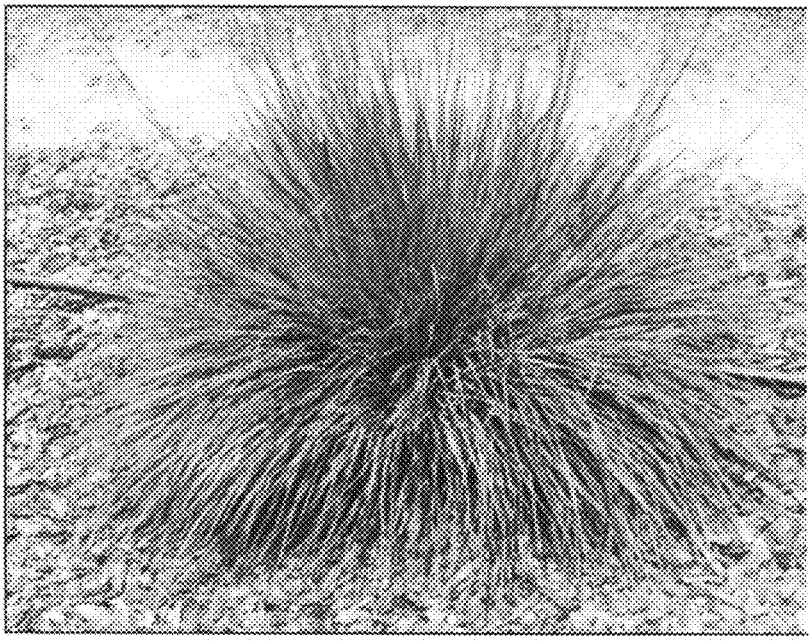
Figure 12:
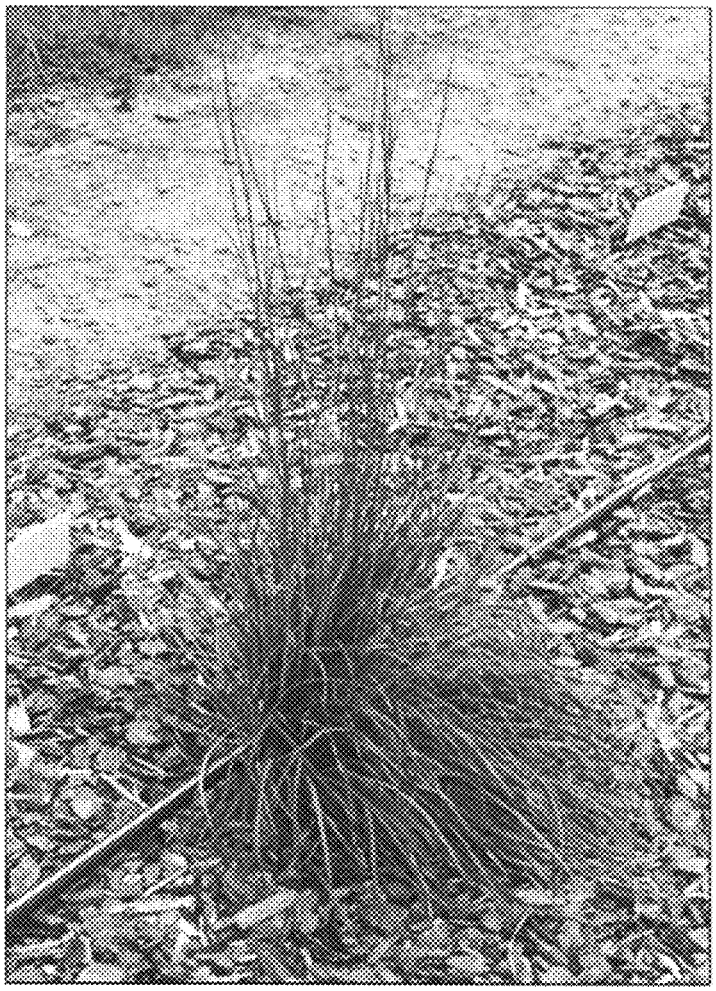
FIGS. 12 and 13 are photographs of a 'Good Vibrations' plant taken on Aug. 22, 2012 in Griffin, Ga.; with FIG. 13 being an enlarged view.
Figure 13:
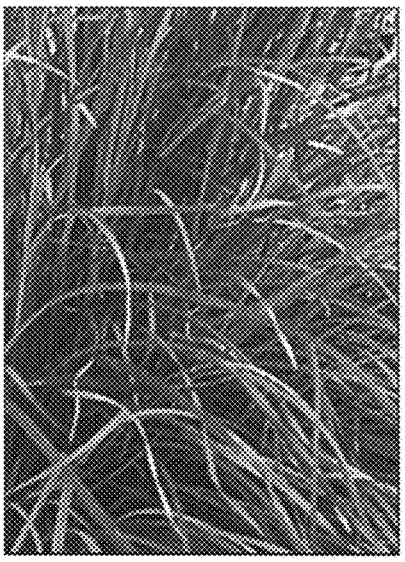

The new variety 'Good Vibrations' is a perennial at Griffin, Ga. (USDA Zone 8a). The new variety 'Good Vibrations' blooms from mid-July to early August. 'Good Vibrations' is drought tolerant and is expected to be able to be grown in USDA Zones 3-9. 'Good Vibrations' grows well in full sun and in most soils. The foliage is fine-textured and long-lived. It appears to be genetically stable and has been asexually propagated by root division. The reproductive organs of the new variety 'Good Vibrations' are very small, fleeting or scarce in presence and therefore difficult to describe.

All data are from four-year-old field-grown plants established as single stem propagules in May 2011, in Griffin, Ga. Three replicated plants were grown in a randomized block design.

Plant:

*Mature plant height*.—Approximately 82 to 98 cm.

*Diameter of plant canopy*.—Approximately 31 to 50 cm.

*Foliage height*.—Approximately 40 to 42 cm.

Leaf:

*Leaf shape*.—Linear.

*Leaf division*.—Simple.

*Leaf margins*.—Entire.

*Leaf base*.—Sheathed to base of culm.

*Leaf venation*.—Parallel, color similar to foliage.

*Leaf apex*.—Acute.

*Leaf arrangement*.—Alternate, 2-ranked.

*Leaf collar type*.—Continuous.

*Leaf persistence*.—Dries but persistent through winter.

*Leaf attachment*.—Sheathed, 1 mm wide membranous ligule.

*Leaf width*.—Approximately 2.25 mm at base and 3 mm on blade.

*Leaf length*.—Approximately 30 cm.

*Leaf number*.—5 to 7 leaves per culm.

*Leaf surface*.—Strigillose, covered in very short hairs that lay nearly flat against the blade and point from to base to tip. Not waxy. Villous sheathes.

*Adaxial leaf surface trichomes*.—None.

*Abaxial leaf surface trichomes*.—None.

*Sheath trichomes*.—None.

*Adaxial leaf color*.—Early Summer: Green 137C or 138B or Purple N77A at the basal end changing to Violet-Blue N92D at the terminal end. Mid-Summer: Basal portion of the leaf is Green 138B, changing to Greyed-Purple N186A, N186B, or N186C on the distal portion; or basal portion is Green 138B changing to Greyed-Purple 187A at the distal portion; or basal portion is Green 138B changing to Purple N77C at the distal portion. Late Summer (displays a mix of color types): Yellow-Green 144A; or Greyed-Purple N186C; Greyed-Purple 183C. Early Fall: Green 138A or 138B; or Greyed-Purple 187A; or Purple N79B.

*Abaxial leaf color*.—Early Summer: Green 138B or 138C; or Purple N77C. Mid-Summer: Green 138B. Later Summer (displays a mix of color type): Greyed-Green 191B; or Greyed-Purple N187B; or Greyed-Purple 183D. Early Fall: Green 138B or Purple N77C.

Flower:

*Blooming period*.—Mid July to early August in Griffin, Ga. with multiple racemes present. per flower culm.

*Inflorescence*.—Yes.

*Inflorescence type*.—Racemes at terminus and nodes.

*Inflorescence size*.—2 to 7 cm in length, 0.5 cm in diameter.

*Inflorescence color*.—Red-Purple 59B.

*Spikelet*.—Number 5 to 10 per raceme.

*Spikelet size*.—2 to 7 cm long and with an internode distance of 2 cm.

*Spikelet arrangement*.—Alternately on the rachis.

*Spikelet hairs*.—Approximately 1 to 2 mm long, White N155D with a fluffy texture.

*Glumes*.—Average of 6 mm long by 1 mm wide.

*Palea*.—1 mm long and less than 1 mm wide.

*Peduncle*.—1 to 7 cm long and 1 mm diameter.

*Peduncle color*.—Greyed-Orange 174A.

Culm:

*General*.—Flat, solid.

*Stem surface*.—Strigillose, less toward the base, becoming more numerous on the blade.

*Pith*.—1 mm wide, Yellow-Green 153C.

*Culm color*.—Red-Purple 70C toward the base, changing to Green 138B at the terminal portion.

*Culm size*.—5 mm diameter and 5 to 11 cm in length before the blade emerges; at blooming, up to 98 cm from the base to the tip of the flower panicle.

*Internode length*.—7 cm.

*Style*.—1 mm long, plumose, Red-Purple 61A.

What is claimed is:

1. A new and distinct variety of the *Schizachyrium* plant named 'Good Vibrations' as herein illustrated and described.

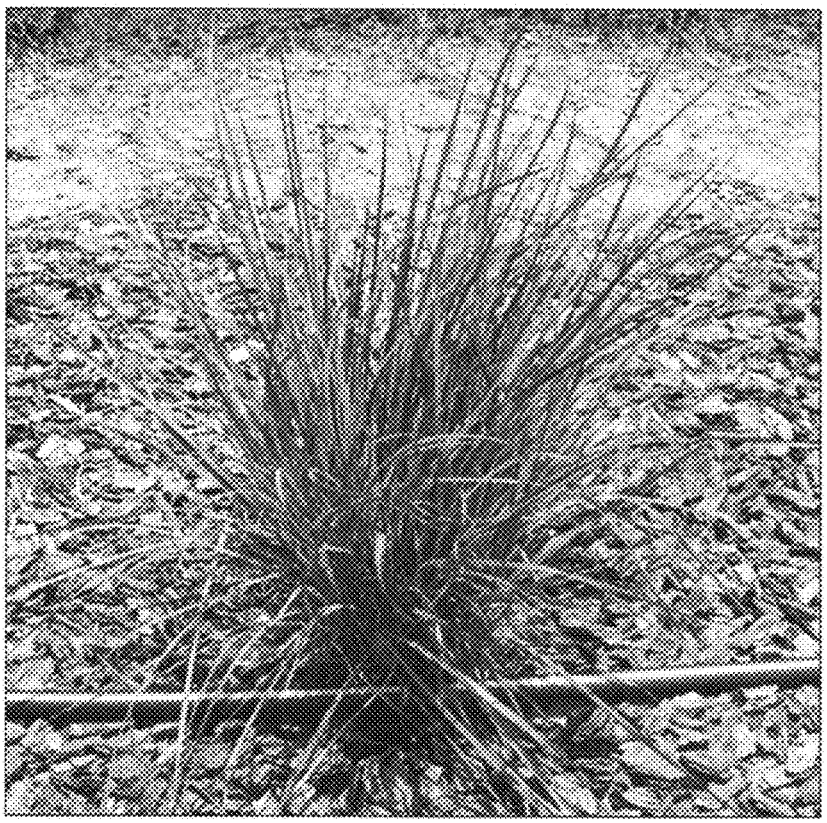
FIG. 4
FIG. 5
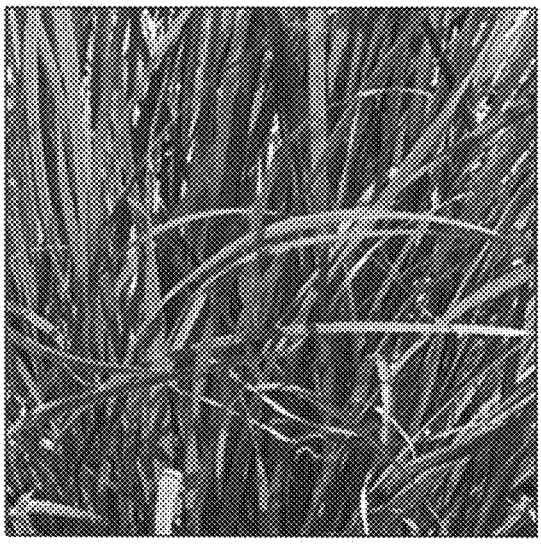

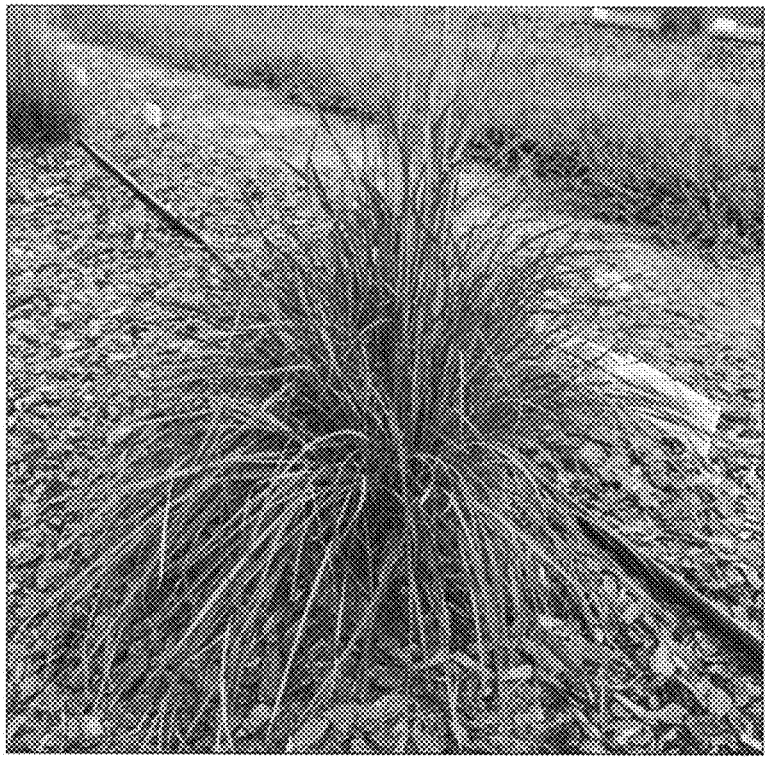
FIG. 8
FIG. 9
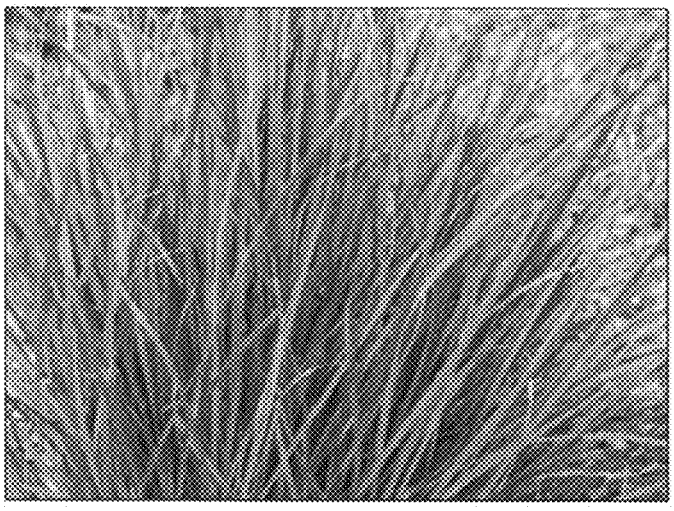

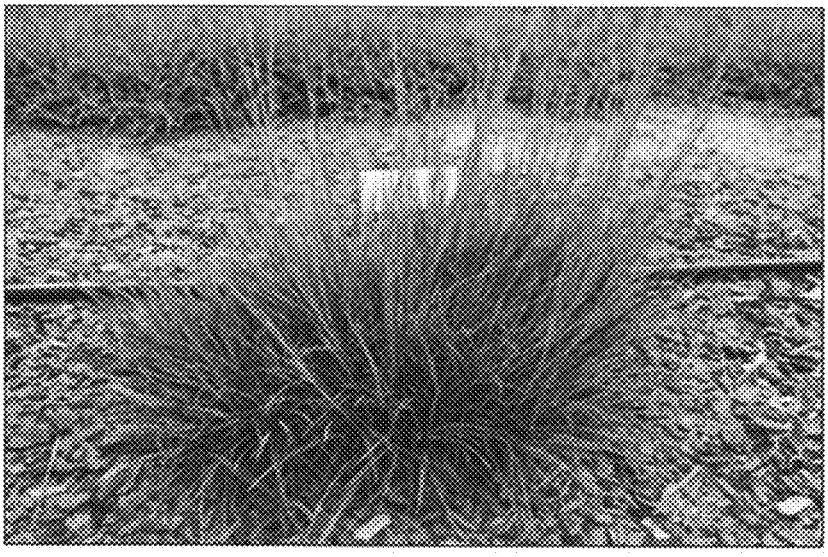
FIG. 10
FIG. 11
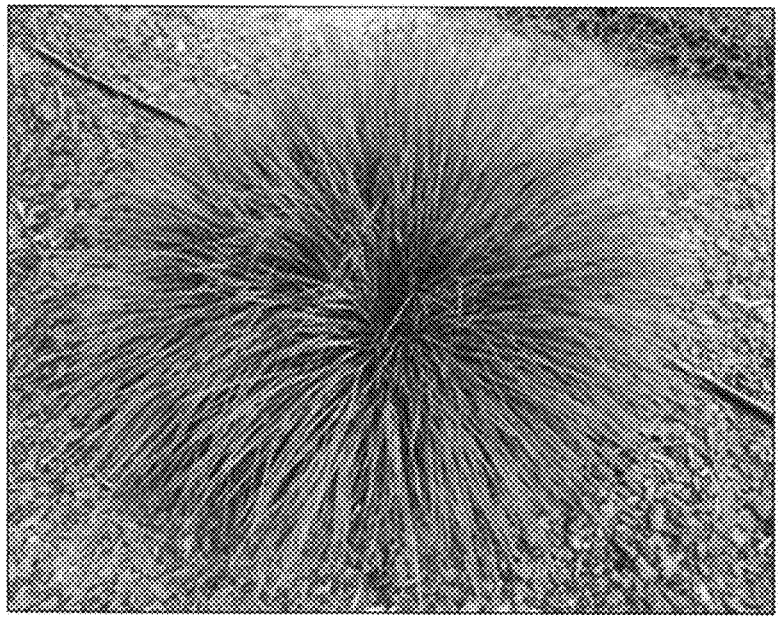

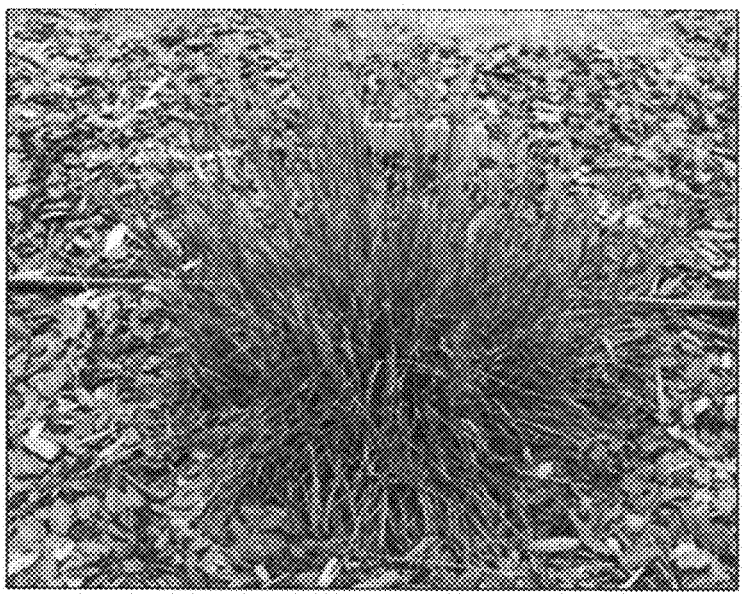
FIG. 14
FIG. 15
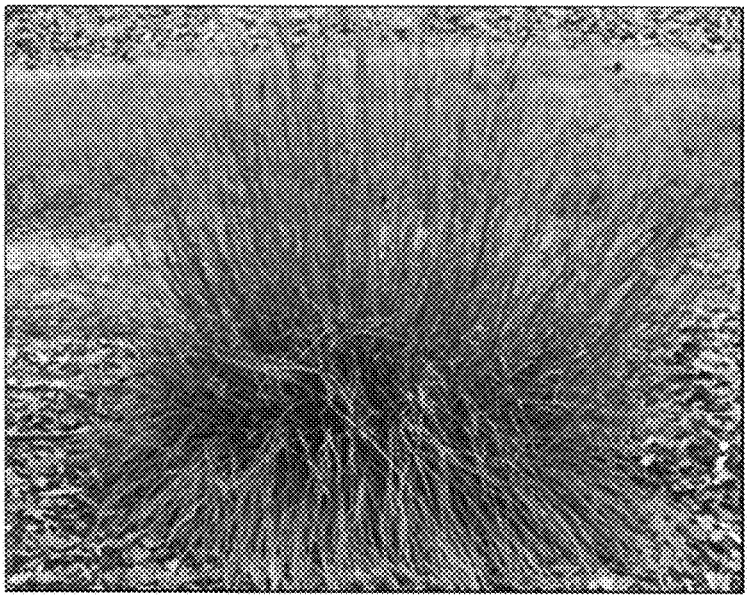

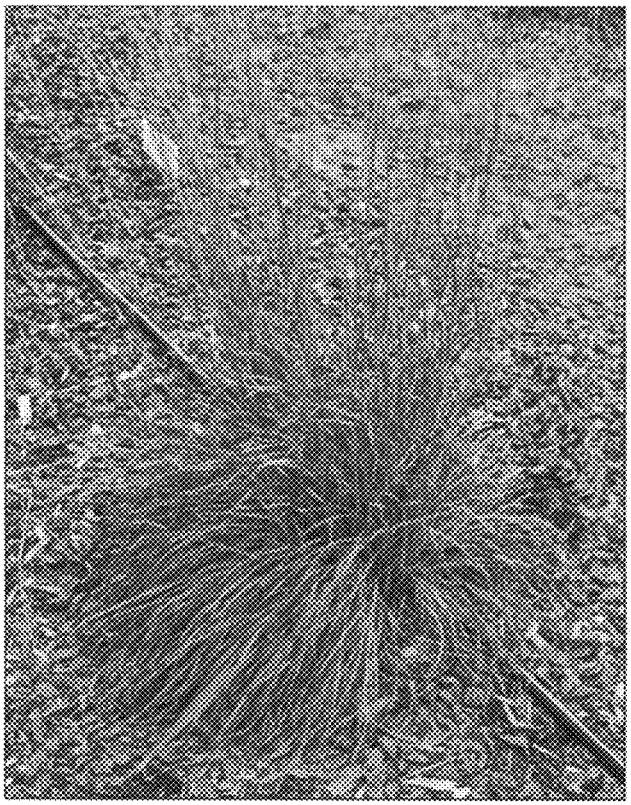
FIG. 16
FIG. 17
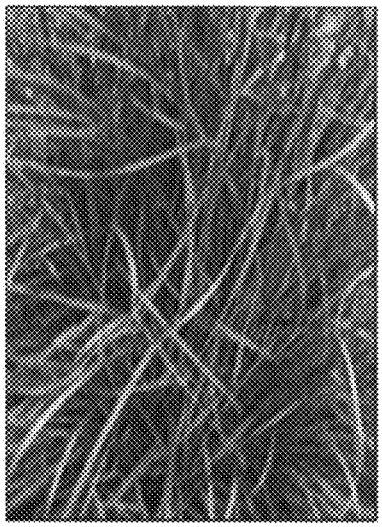

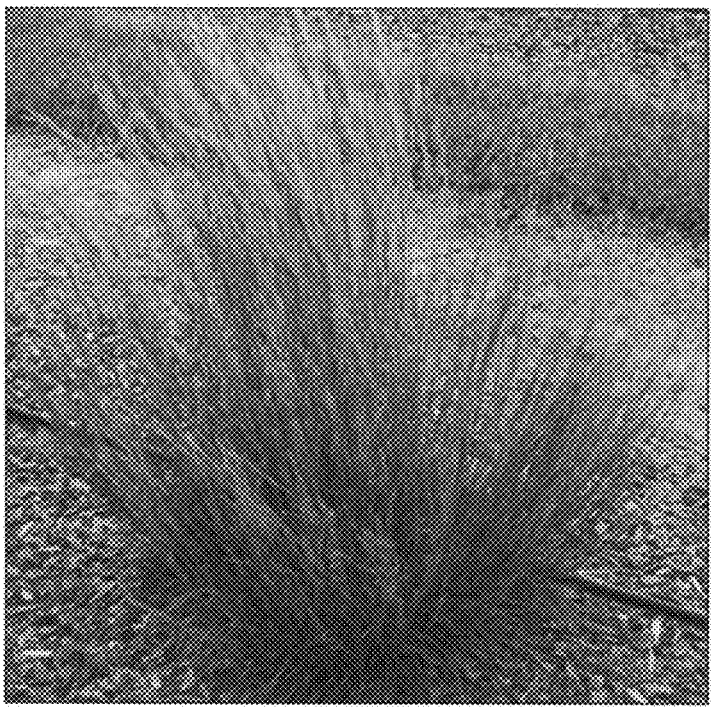
FIG. 18
FIG. 19
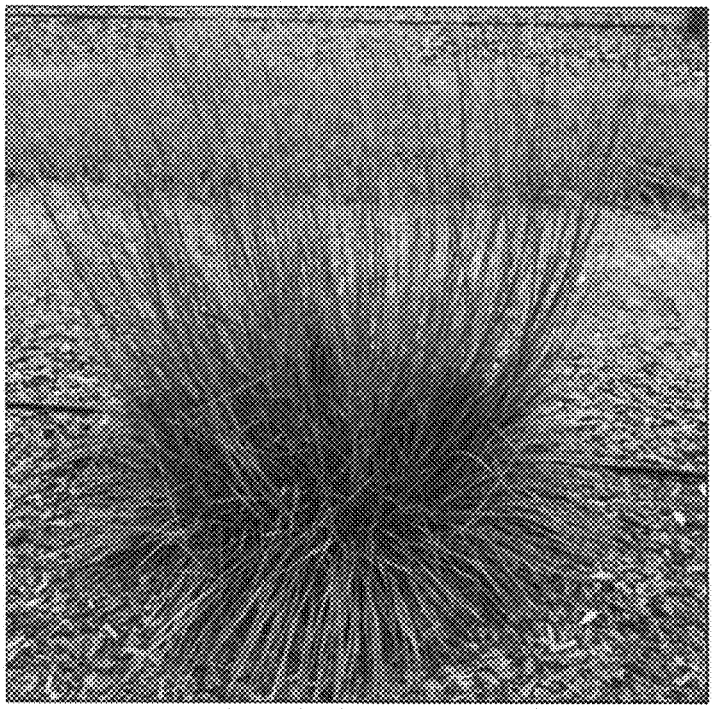

* * * * *